United States Patent [19]

Barton et al.

[11] 4,257,428
[45] * Mar. 24, 1981

[54] RETRACTABLE STIMULATION ELECTRODE APPARATUS AND METHOD

[76] Inventors: Steven A. Barton, 401 S. Brazosport Blvd., Freeport, Tex. 77541; Steven G. Anderson, 107 Poinciana St., Lake Jackson, Tex. 77566

[*] Notice: The portion of the term of this patent subsequent to Jan. 30, 1997, has been disclaimed.

[21] Appl. No.: 951,726

[22] Filed: Oct. 16, 1978

Related U.S. Application Data

[63] Continuation-in-part of Ser. No. 858,954, Dec. 9, 1977, Pat. No. 4,136,701.

[51] Int. Cl.³ .............................................. A61N 1/04
[52] U.S. Cl. .................................................. 128/785
[58] Field of Search ................. 128/419 P, 783, 784, 128/785, 790

[56] References Cited

U.S. PATENT DOCUMENTS

| | | | |
|---|---|---|---|
| 3,472,234 | 10/1969 | Tachick | 128/785 |
| 3,745,555 | 8/1973 | Schmitt | 128/785 |
| 3,814,104 | 6/1974 | Irnich et al. | 128/785 |
| 3,844,292 | 10/1974 | Bolduc | 128/785 |
| 3,902,501 | 9/1975 | Citron et al. | 128/785 |
| 3,974,834 | 8/1976 | Kane | 128/785 |
| 4,011,875 | 3/1977 | Lehr et al. | 128/785 |
| 4,103,690 | 8/1978 | Harris | 128/785 |
| 4,106,512 | 8/1978 | Bisping | 128/785 |
| 4,136,701 | 1/1979 | Barton et al. | 128/785 |

FOREIGN PATENT DOCUMENTS

2539553  3/1977  Fed. Rep. of Germany ........... 128/785

*Primary Examiner*—William E. Kamm
*Attorney, Agent, or Firm*—Jones, Thomas & Askew

[57] ABSTRACT

Electrode apparatus which is used with stimulation devices, such as cardiac pacemakers or the like. Two or more tissue-engaging members are retractably mounted within the electrode apparatus. The tissue-engaging members are extended to engage body tissue and retracted while maintaining engagement with the body tissue, to thereby bring the body tissue into predetermined signal transfer contact with the conductive portion of the electrode body. Retraction or extension of the tissue-engaging member is accomplished with an elongate tool which is extendable through the hollow coil that attaches to the body of the electrode apparatus. A spring within the electrode body facilitates retraction of the tissue-engaging member.

7 Claims, 8 Drawing Figures

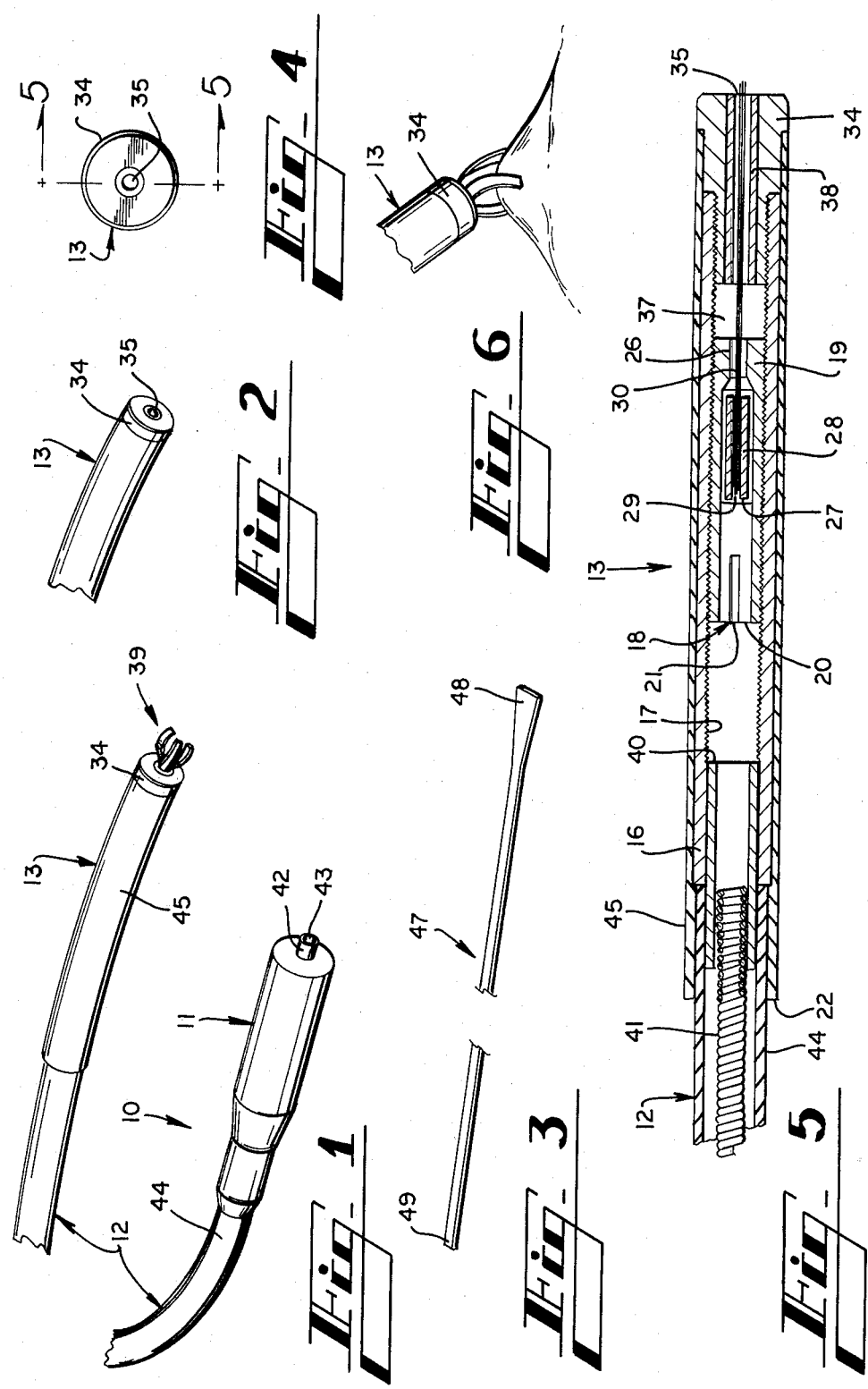

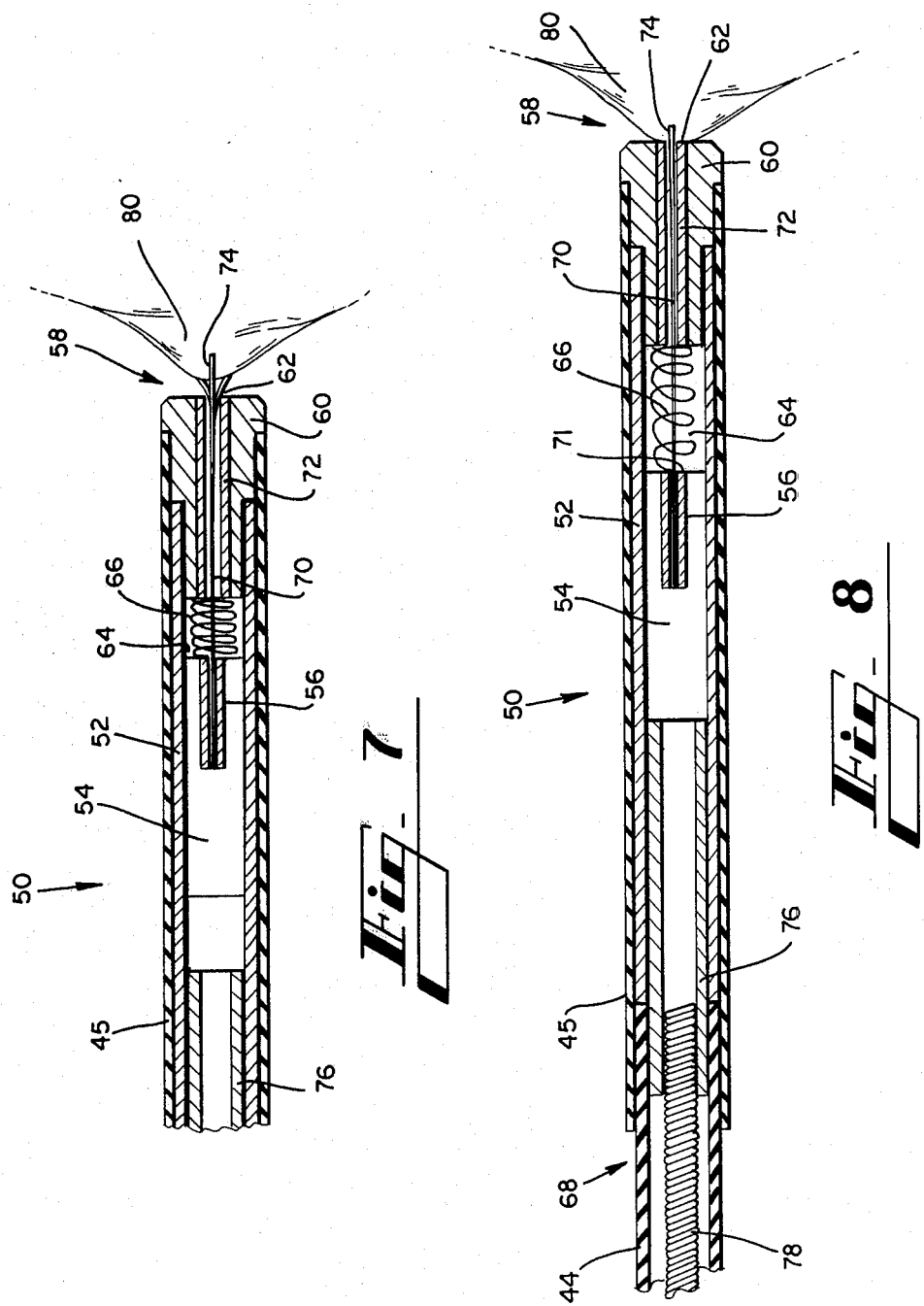

RETRACTABLE STIMULATION ELECTRODE APPARATUS AND METHOD

DESCRIPTION

CROSS-REFERENCE TO RELATED APPLICATION

This is a continuation-in-part of Ser. No. 858,954 filed Dec. 9, 1977 now U.S. Pat. No. 4,136,701.

TECHNICAL FIELD

This invention relates in general to body tissue stimulation apparatus and in particular to electrode apparatus intended for use with tissue stimulating devices such as cardiac pacemakers or the like.

Pacemakers and other tissue stimulation devices generally operate to provide an electrical signal which is applied to certain body tissue so as to stimulate or otherwise affect the operation of an organ of the body. The actual stimulation signals are typically generated by a pacemaker or other apparatus which may be surgically implanted within the body, but not in direct contact with the heart or other organ to be regulated, and suitable electrical leads must then be provided to supply the signals from the electronic device to the particular organ of the body.

BACKGROUND ART

A critical portion of such body electrodes is the element which actually contacts or engages the body tissue to make electrical signal-transfer contact therewith. Some body tissue leads used for pacemaking purposes rely on an electrode having an enlarged tissue-contacting tip having a blunt or spherical configuration, devoid of any projections or other sharp edges which might cause damage to body tissue. Such electrodes must be firmly positioned against the appropriate location on a body organ, e.g., the heart, and must in some manner be maintained in the desired position, since there is no mechanical engagement of the blunt electrode end with the body tissue. As a consequence, there is a risk that such body-implantable leads of the prior art can become dislocated so as to move out of signal-transfer contact with the desired area of body tissue, such as by active movement of the body or the like.

Another type of prior-art electrical lead includes relatively pointed electrode members which can project into the surface of the desired body tissue, thereby providing a degree of physical engagement between the electrode and the body tissue. It has been found that such pointed electrodes may cause unwanted and unnecessary tissue damage, however, especially when it becomes necessary for a surgeon to reposition the electrode within the body, since such electrodes as used in cardiac pacemaker applications are frequently inserted through a patient's vein with a catheter. Venous repositioning of prior-art electrodes having tissue-engaging pointed members may be sufficiently damaging that it becomes necessary to surgically remove or reposition the electrode by opening up the chest cavity of the patient. The time, trauma, and expense of such a procedure is self-evident.

Accordingly, it is an object of the present invention to provide an improved electrode apparatus for tissue stimulation.

It is another object of the present invention to provide stimulation electrode apparatus having tissue-engaging members which can be repositioned with relatively little or no tissue damage.

It is yet another object of the present invention to provide body implantable electrode apparatus having tissue-engaging members that are selectably retractable into or extendable from the electrode assembly.

It is a further object of the present invention to provide stimulation electrode apparatus having tissue-engaging members which grasp or pinch body tissue to thereby establish a firm hold on said body tissue so as to draw said body tissue into positive signal transfer contact with the electrode tip when said tissue-engaging members are retracted.

Another object of the present invention is to provide stimulation electrode apparatus having a member for facilitating the retraction of the tissue-engaging members.

Another object of the present invention is to provide an improved method for establishing electrical signal communication between body tissue and an electrode.

SUMMARY OF THE INVENTION

Stated in general terms, the electrode apparatus of the present invention comprises an electrode body portion which is connected to a pacemaker or other utilization device by an electrical lead having a hollow passageway along its length, so as to accommodate a manipulating tool. Within the electrode body portion of the apparatus is a movable member which is engagable by the tool when extended through the lead. The movable member within the electrode body of the electrode is connected with two or more tissue-engaging members which are extendable out of the electrode body or retractable into the electrode body in response to manipulation of the movable member by the tool extended through the passage of the lead. Stated somewhat more specifically, the movable member in one embodiment of the invention engages threads within the electrode body to reciprocate within the body in response to being rotated by a tool extended through the lead. It is this reciprocation of the movable member which selectably extends or retracts the tissue-engaging members relative to the electrode body. A rotating connection is provided between the rotatable member of the electrode body and the tissue-engaging members, so that the tissue-engaging members do not rotate as such members are being extended or retracted relative to the electrode body. The tissue-engaging member may be extended to engage body tissue, whereupon the tissue-engaging members grasp or pinch the body tissue to thereby establish a firm hold thereon. The tissue engaging members may then be non-rotatingly retracted while maintaining engagement with the body tissue to thereby bring the body tissue into predetermined signal transfer contact with a conductive portion of the electrode body.

In another embodiment of the present invention the movable member is slidably disposed within the electrode body. A spring member, or the like, maintains the movable member and the tissue-engaging members attached thereto in a retracted position. The movable member may be reciprocated within the electrode body to selectably extend or retract the tissue-engaging members by reciprocal movement of a tool extended through the lead to engage the movable member and displace the movable member against the resistive force of the spring member.

The nature of the present invention as well as other objects and advantages thereof will be more readily apparent from the following discussion of the disclosed embodiment thereof, as shown in the drawing.

BRIEF DESCRIPTION OF THE DRAWINGS

FIG. 1 is a broken pictorial view showing a disclosed embodiment of the present invention, with tissue-engaging members depicted in extended position;

FIG. 2 is a fragmentary pictorial view of the embodiment shown in FIG. 1, with the tissue-engaging members retracted into the electrode body;

FIG. 3 is a broken pictorial view showing an embodiment of the tool which is used in combination with the disclosed embodiments of the present invention;

FIG. 4 is an end elevation view showing the electrode body of a disclosed embodiment; and FIG. 5 is a cross-sectional view taken alone line 5—5 of the electrode body shown in FIG. 4.

FIG. 6 is a detailed view of the electrode tip and the tissue-engaging members shown in FIG. 1 shown engaging body tissue.

FIG. 7 is a cross-sectional view of an alternate disclosed embodiment of the electrode body of the present invention showing the tissue-engaging members in an extended position.

FIG. 8 is a cross-sectional view of the alternate disclosed embodiment shown in FIG. 7, showing the tissue-engaging members in a retracted position.

DETAILED DESCRIPTION OF THE DISCLOSED EMBODIMENT

Turning to the drawing, there is shown generally at 10 an embodiment of an electrode apparatus according to the teachings of the present invention. The electrode apparatus 10 includes a connector member 11 designed for attachment to a signal device such as a cardiac pacemaker or the like, a lead portion 12, and an electrode body 13 which is intended to be positioned in proximate relation to the organ to be stimulated. It will be understood by those skilled in the art that all exposed surfaces of the electrode apparatus 10 are constructed of materials such as stainless steel, silicone rubber, or other materials which do not react with the body of the recipient patient and which are not damaged by exposure to body fluids.

Details of the electrode body 13 are best seen in FIGS. 4 and 5. The electrode body includes an elongate hollow barrel 16 which is threaded as at 17 along at least a portion of its open interior. Received within the hollow barrel 16 is a movable slug assembly 18, which includes a hollow tube 19 and a closure 20 which is press-fit or otherwise secured into the open end of the hollow tube facing toward a lead-connecting end 22 of the electrode body 13. The exterior of the hollow tube 19 has threads which mate with the threads 17 on the interior of the barrel 16, and the closure 20 is provided with suitable tool-engaging structure, such as an open slot 21, which faces toward the lead-connecting end 22 of the electrode body 13. The interior diameter of the hollow tube 19 is reduced toward the tip-confronting end of the tube to provide a relatively narrow aperture 26, so that a chamber 27 is defined within the hollow tube between the aforementioned aperture and the inwardly facing end of the closure 20. Loosely received within the chamber 27 is a hollow tube 28, and ends 29 of three flat spring members 30 are secured to the tube 28 within its interior by means of brazing or by any other suitable securement technique. The flat spring members 30 are made of a material which may be deformed from a predetermined configuration by applying a force and then return to the predetermined configuration upon release of the force. Additionally, the flat spring members 30 are made from material which does not react with the body of the recipient patient and which are not damaged by exposure to body fluids. The tube 28 should be received within the chamber 27 with enough play so that the tube can remain in non-rotating relation to the hollow tube 19, when the latter is rotated. It may be desirable to coat the exterior of the tube 28 with a small amount of oil or another suitable lubricant during assembly of the electrode body 13, so as to facilitate the rotation of the hollow tube 19 relative to the tube 28.

Fixed in the forward end of the barrel 16 is a hollow conductive electrode tip 34 having an opening 35 therein. The spring members 30 extend through the aperture 26 in the forward end of the hollow tube 19, through a chamber 37 defined by the barrel 16 between the hollow tube 19 and the tip 34 and outwardly through the opening 35 in the tip 34. The tip 34 has a hollow tube 38 secured within, in coaxial alignment with the aperture 26 in the hollow tube 19, so that the tube 38 provides lateral support and guidance for the spring members 30.

The outer ends 39 of the spring members 30 comprise the tissue-engaging members of the electrode apparatus 10. The ends 39 of the spring members 30 are of a slightly curved shape, and are approximately equally radially separated from each other when in an extended position (FIG. 1). The curved ends 39 thereby form finger-like projections extending from the tip 34. The function of the ends 39 will be apparent as described in more detail hereinbelow.

A hollow tube 40 is secured within the interior of the barrel 16 at the lead-connecting end 22 thereof, and a hollow, flexible, electrically-conductive coil 41 is firmly secured within the hollow tube 40. The coil 41, which is preferably made of a material such as stainless steel, Elgiloy (a trademark of Elgin Watch Company), or the like, extends along the length of the lead 12 and is attached to a hollow connector pin 42 (FIG. 1) of the connector member 11. It will be understood that an opening 43 into the hollow connector pin 42 is coaxially aligned with the hollow interior or lumen of the coil 41.

The coil 41 is received within a sheath 44 of a suitable fluid-impervious flexible and electrically-insulating material such as silicone rubber or the like, which is bonded to a sleeve 45 of like or similar material which encloses the barrel 16 and other components of the electrode body 13. It will be understood that the exterior of the connector member 11 is also fabricated from a similar material which is bonded or otherwise secured to the sheath 44 of the lead 12.

The operation of the disclosed embodiment will now be considered. It will be seen that the outer ends 39 of the spring members 30 may be extended outwardly from the tip 34 to be in a tissue-engaging position as shown in FIG. 1, or may be withdrawn within the opening 35 of the electrode body tip 34 to be in a retracted position as shown in FIG. 2, depending on the logitudinal position of the slug assembly 18 within the barrel 16 of the electrode body. It is assumed that the slug 18 will be rotated within the barrel 16 so to move toward the end 22 of the electrode body and thereby to withdraw the outer ends 36 of the spring members 30, before the electrode apparatus 10 is initially inserted into a patient's body by venous passage or otherwise. Once the surgeon decides that the tip 34 of the electrode body is appropriately positioned adjacent the heart, or some other organ of the body, an appropriate tool such as the screwdriver stylet 47 (FIG. 3) is inserted through the opening 43 in the pin 42 so as to extend through the hollow coil 41 and into the hollow interior of the electrode body barrel 16. The stylet 47, which is sufficiently flexible to follow the contour of the lead 12, has a forward end 48 forming a screwdriver tip which is receivable within the slot 21 formed in the closure 20. The tube 40 guides the forward end 48 of the stylet toward the slot 21, in addition to defining a motion stop for the slug 18. The stylet 47 is sufficiently long to permit the back end 49 thereof to extend out of the opening 43 in the pin 42. After insertion in the slot 24 the stylet may be rotated so as to rotate the slug 18, thereby longitudinally moving the slug toward the tip 34 of the electrode body 13.

Forward movement of the slug 18 moves the tube 28 forwardly, causing the outer ends 39 of the spring members 30 to extend outwardly from the tip 34. It will be noted that due to the curved nature of the ends 39 of the spring members 30, the ends, which are squeezed together within the tube 38 so that the tips of the ends are touching when the ends are retracted within the tip 33, spring outwardly from each other so as to provide spaces between the tips of the ends when the ends are extended from the tip 34. Thus, when the ends 39 of the spring members 30 are in the extended position, adjacent body tissue will protrude into the spaces between the tips of the ends of the spring members.

To attach the electrode apparatus 10 to the body tissue, the stylet 47 is rotated so as to rotate the slug 18, thereby longitudinally moving the slug toward the end 22 of the electrode body to retract the spring members 30 and the ends 39 thereof into the tip 34. As the ends 39 of the spring members 30 begin to retract, the tips of the ends begin to come together thereby grasping or pinching body tissue 46 therebetween (FIG. 6). As the ends 39 retract further into the tip 34, the tissue 46 continues to be pinched or engaged by the ends of the spring members 30 and the tissue is drawn toward the tip 34 of the electrode apparatus 10. When the ends 39 of the spring members 30 are sufficiently retracted into the tip 34, the body tissue 46 will be held in contact with the tip of the electrode for stimulation thereby. Installation of the electrode apparatus is completed by withdrawing the stylet 47, so that the connector member 11 can be attached to a pacemaker or other suitable electronic apparatus.

It will be appreciated by those skilled in the art that the electrode of the present invention may be fixed in position and held in position without causing damage to the body tissue with sharp, pointed electrodes used in tissue penetration type electrodes.

If it is desired to reposition the electrode apparatus within the body of the recipient patient, or to entirely withdraw the electrode apparatus from the body of the recipient patient, the stylet 47 is again inserted through the lead 12 to operatively engage the slug 18. The slug is then rotated in the proper direction by the stylet to extend the outer ends 39 of the spring members from the tip 34 to release the pinched body tissue and then retract the ends within the tip 34 during removal or repositioning of the electrode apparatus 10. The aforementioned non-rotating relation between the tube 28 and the slug 18 allows the tissue-engaging members to be extended and withdrawn without rotation of the ends 39, thereby minimizing tissue damage which would otherwise occur if the ends 39 were rotated while engaged with body tissue. Similarly, the tissue-engaging ends 39 may be non-rotatably extended and retracted after the electrode body 13 has been repositioned within the patient's body.

Referring now specifically to FIGS. 7 and 8, it will be seen that there is an alternate embodiment of the electrode body of the present invention. There is shown an electrode body 50 which includes an elongate hollow barrel 52. Received within the hollow barrel 52 is a movable slug 54 having a hollow tube 56 secured in the end of the slug which faces the tissue-engaging end 58 of the electrode body 50. The exterior surface of the slug 54 is smooth or even for sliding contact with the interior surface of the barrel 52 which is likewise smooth and even. It may be desirable to coat the exterior surface of the slug 54 and the interior surface of the barrel 52 with a small amount of oil or another suitable lubricant during assembly of the electrode body 50, so as to facilitate the sliding of the slug within the barrel.

Fixed in the forward end of the barrel 52 is a hollow conductive electrode tip 60 having an opening 62 therein. A chamber 64 is defined by the barrel 52 between the slug 54 and the electrode tip 60. A compression spring 66 occupies the chamber 64. The spring 66 exerts a force on the slug 54 tending to urge the slug in a direction toward the lead connecting end 68 of the electrode body 50.

Secured within the hollow tube 56 are three flat spring members 70. The ends of the spring members 70 are secured within the tube 56 by means of brazing or by any other suitable securement technique. The spring members 70 extend through an aperture 71 in the forward end of the hollow tube 56, through the center of the coiled compression spring 66 and outwardly through the opening 62 in the tip 60. The tip 60 has a hollow tube 72 secured within, in coaxial alignment with the aperture 71 in the hollow tube 56, so that the tube 72 provides lateral support and guidance for the spring members 70.

The outer ends 74 of the spring members 70 comprise the tissue-engaging members of the electrode apparatus. The ends 74 of the spring members 70 are of a slightly curved shape, and are approximately equally radially separated from each other when in an extended position. The curved ends 74 thereby form finger-like projections extending from the tip 60. The function of the ends 74 will be apparent as described in more detail hereinbelow.

A hollow tube 76 is secured within the interior of the barrel 52 at the lead-connecting end 68 thereof, and a hollow, flexible, electrically-conductive coil 78 is firmly secured within the hollow tube 76. It will be appreciated that the hollow tube 76 also functions as a motion stop which limits the rearward motion of the slug 54, although other structure can be disposed within the barrel 52 to function as a motion stop for the slug. The coil 78, which is preferably made of a material such as stainless steel, Elgiloy (a trademark of Elgin Watch Company), or the like, extends along the length of the lead 12 and is attached to a hollow connector pin 42 (FIG. 1) of the connector member 11. It will be understood that an opening 43 into the hollow connector pin 42 is coaxially aligned with the hollow interior or lumen of the coil 78.

The coil 78 is received within a sheath 44 of a suitable fluid-impervious flexible and electrically-insulating material such as silicone rubber or the like, which is bonded to a sleeve 45 of like or similar material which encloses the barrel 52 and other components of the electrode body 50. It will be understood that the exterior of the connector member 11 is also fabricated from a similar material which is bonded or otherwise secured to the sheath 44 of the lead 12.

The operation of the alternate disclosed embodiment will now be considered. It will be seen that the outer ends 74 of the spring members 70 may be extended outwardly from the tip 60 to be in a tissue-engaging position as shown in FIG. 7, or may be withdrawn within the opening 62 of the electrode body tip 60 to be in a retracted position as shown in FIG. 8, depending on the longitudinal position of the slug 54 within the barrel 52 of the electrode body 50. Since the spring 66 exerts a rearward force on the slug 54, the slug is nominally resting against the hollow tube 76 (FIG. 8). In this position the outer ends 74 of the spring member 70 are withdrawn within the tip 60 before the electrode apparatus is initially inserted into a patient's body by venous passage or otherwise. Once the surgeon decides that the tip 60 of the electrode body is appropriately positioned adjacent the heart, or some other organ of the body, an appropriate tool such as the stylet 47 (FIG. 3) is inserted through the opening 43 in the pin 42 so as to extend through the hollow coil 78 and into the hollow interior of the electrode body barrel 52. The stylet 47, which is sufficiently flexible to follow the contour of the lead 12, has a forward end 48 forming a tip. The tube 76 guides the forward end 48 of the stylet toward the rear surface of the slug 54. The stylet 47 is sufficiently long to permit the back end 49 thereof to extend out of the opening 43 in the pin 42 when the forward end 48 of the stylet is in engagement with the slug 54. After contacting the rear surface of the slug 54, the stylet may be extended forward slightly further, thereby longitudinally moving the slug toward the tip 60 of the electrode body 50 and compressing the spring 66.

Forward movement of the slug 54 causes the outer ends 74 of the spring members 70 to extend outwardly from the tip 60. It will be noted that due to the curved nature of the ends 74 of the spring members 70, the ends, which are squeezed together within the tube 72, so that the tips of the ends are touching when the ends are retracted within the tip 60, spring outwardly from each other so as to provide spaces between the tips of the ends when the ends are extended from the tip 60. Thus, when the ends 74 of the spring members 70 are in the extended position, adjacent body tissue will protrude into the spaces between the tips of the ends of the spring members.

To attach the electrode apparatus to the body tissue, forward pressure on the stylet 47 is relaxed slightly to permit the compressed spring 66 to longitudinally slide the slug 54 toward the end 68 of the electrode body and thereby retract the spring members 70 and the ends 74 thereof into the tip 60. As the ends 74 of the spring members 70 begin to retract, the tips of the ends begin to come together, thereby grasping or pinching body tissue 80 therebetween (FIG. 7). As the ends 74 retract further into the tip 60, the tissue 80 continues to be pinched or engaged by the ends of the spring members 70 and the tissue is drawn toward the tip 60 of the electrode body 50. When the ends 74 of the spring members 70 are sufficiently retracted into the tip 60, the body tissue 80 will be held in contact with the tip of the electrode for stimulation thereby (FIG. 8). Installation of the electrode apparatus is completed by withdrawal of the stylet 47, so that the connector member 11 can be attached to a pacemaker or other suitable electronic apparatus.

If it is desired to reposition the electrode apparatus within the body of the recipient patient, or to entirely withdraw the electrode apparatus from the body of the recipient patient, the stylet 47 is again inserted through the lead 12 to operatively engage the slug 54. Forward pressure is exerted on the slug 54 by the stylet 47 to extend the outer ends 74 of the spring members 70 from the tip 60 to release the pinched body tissue. The ends 74 may then be retracted within the tip 60 during removal or repositioning of the electrode apparatus by releasing the forward pressure exerted by the stylet on the slug 54, thereby permitting the spring 66 to return the slug to its normal position.

It will be appreciated by those skilled in the art that since the slug 54 is not rotated to extend or retract the ends 74 of the spring members 70, neither do the ends 74 rotate during extension and retraction. Tissue damage which would otherwise occur if the ends 74 were rotated while engaged with body tissue is thereby minimized.

It should be understood that although the present invention has been disclosed as having three spring members which constitute the tissue-engaging members, that any suitable number of two or more such tissue-engaging members may be used. An essential feature of the tissue-engaging members is the pinching or grasping effect brought about by the closable and opposable feature of the spring members. This effect is similar to the pinching or grasping ability of the opposable thumb and fingers of the human hand. It will therefore be appreciated that other numbers of tissue-engaging members may be used in the present invention.

It will be apparent that the foregoing relates only to disclosed embodiments of the present invention, and that numerous alterations and modifications may be made therein without departing from the spirit and the scope of the following claims.

I claim:

1. Retractable tissue-engaging electrode apparatus, comprising:

an electrically conductive signal lead means;

electrode body means connected to said signal lead means and having a conductive portion intended for signal transfer contact with body tissue;

tissue-engaging means associated with said electrode body means and operative to selectively engage body tissue, said tissue-engaging means having an extended position and a retracted position and being operative to pinchingly engage body tissue with sufficient force to move said body tissue and said conductive portion into mutual engagement as said tissue-engaging means is moved from said extended position toward said retracted position; and means within said electrode body means and operatively associated with said tissue-engaging means to selectably place said tissue-engaging means in either said extended position or said retracted position, so as to selectively pinchingly engage said body tissue.

2. Apparatus of claim 1, wherein said tissue-engaging means comprises at least two opposable members having ends which are extendable from said electrode body means and which are retractable within said electrode body means, and wherein said ends of said opposable members are spaced apart when extended from said electrode body means and said ends are urged together when retracted within said electrode body means to thereby pinchingly engage said body tissue.

3. Apparatus of claim 2, wherein said electrode body means has a longitudinal axis and wherein said means within said electrode body means comprises means attached to said opposable members and slidably disposed within said electrode body means, said attached means having a first position wherein said opposable members are retracted within said electrode body means and a second position longitudinally displaced from said first position wherein said opposable members are extended from said electrode body means.

4. Apparatus of claim 3 further comprising means for urging said attached means from said second position to said first position.

5. Apparatus of claim 4, wherein said urging means comprises a spring.

6. The method of establishing a selectably releasable electrical signal communication between body tissue and an electrode surface disposed adjacent the body tissue, comprising the steps of:

engaging the body tissue by pinching a portion of the body tissue between a plurality of members; and then nonrotatably moving the plural members toward the electrode surface so as to draw the pinched portion of body tissue and the electrode surface into mutual signal transfer contact.

7. The method of claim 6, wherein said engaging step includes pinching without puncturing the body tissue.

* * * * *